United States Patent [19]

Schohe-Loop et al.

[11] Patent Number: 5,874,438

[45] Date of Patent: Feb. 23, 1999

[54] 2,2'-BRIDGED BIS-2,4-DIAMINOQUINAZOLINES

[75] Inventors: Rudolf Schohe-Loop, Wuppertal; Peter-Rudolf Seidel, Köln; William Bullock; Walter Hübsch, both of Wuppertal; Achim Feurer, Odenthal; Hans-Georg Lerchen, Köln; Georg Terstappen, Düsseldorf; Joachim Schuhmacher, Wuppertal; Franz-Josef van der Staay, Lohmar/Wahlscheid; Bernard Schmidt, Lindlar, all of Germany; Richard J. Fanelli, Madison, Conn.; Jane C. Chisholm, Clinton, Conn.; Richard T. McCarthy, Madison, Conn.

[73] Assignee: Bayer Aktiengesellschaft, Leverkusen, Germany

[21] Appl. No.: 729,128

[22] Filed: Oct. 11, 1996

[51] Int. Cl.[6] ............ A01N 43/54; C07D 401/00; C07D 239/72

[52] U.S. Cl. ............ 514/260; 544/284; 544/291

[58] Field of Search .................. 544/284, 291; 514/260

[56] References Cited

U.S. PATENT DOCUMENTS 3,956,495  5/1976  Lacefield et al. ............ 424/251
4,734,418  3/1988  Yokoyama et al. ............ 514/258

FOREIGN PATENT DOCUMENTS 0 188 094  7/1986  European Pat. Off. .

OTHER PUBLICATIONS

Giardina et al., "Synthesis and $\alpha_1$-Antagonist . . . Tetraamine Disulfides." Eur. J. Med. Chem. (1997), vol. 32, pp. 9–20.

Abstract of J6 1140–568–A (English language).

Eur.J.Med.Chem. 12, 1977, 325 (English language).

*Primary Examiner*—Mukund J. Shah
*Assistant Examiner*—Tamthom T. Ngo
*Attorney, Agent, or Firm*—Sprung Kramer Schaefer & Briscoe

[57] ABSTRACT

The present invention relates to 2,2'-bridged bis-2,4-diaminoquinazolines of the general formula (I):

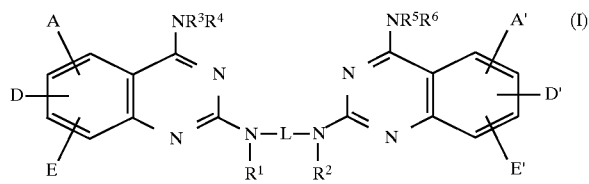

in which the indicated substituents are as defined in the description.

The invention also provides processes for the preparation of the compounds of the formula (I), their use for the preparation of drugs, and drugs containing said compounds.

18 Claims, No Drawings

2,2'-BRIDGED BIS-2,4-DIAMINOQUINAZOLINES

The present invention relates to novel 2,2'-bridged bis-2,4-diaminoquinazolines, to processes for their preparation and to their use in drugs, especially as agents acting on the brain.

4,4'-Diamino-2,2'-piperazinyl-bridged, alkoxy-substituted bisquinazolines and their peripheral action, especially as antihypertensives, are known [cf Jpn. Kokai Tokkyo Koho, JP 61 140 568 and EP 188 094].

The present invention relates to novel 2,2'-bridged bis-2,4-diaminoquinazolines of the general formula (I):

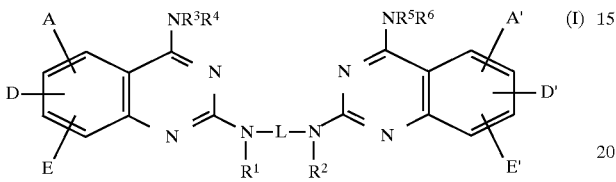

in which

A, A', D, D', E and E' are identical or different and are hydrogen, halogen, hydroxyl, nitro, trifluoromethyl, trifluoromethoxy or linear or branched alkyl or alkoxy, each of which has up to 6 carbon atoms, L is a linear or branched alkylene chain having up to 20 carbon atoms which is optionally interrupted by an oxygen or sulphur atom or by a group of the formula $-NR^7$,
wherein
$R^7$ is hydrogen or linear or branched alkyl having up to 4 carbon atoms, and where the alkylene chain is optionally substituted by up to 3 identical or different substituents selected from hydroxyl, linear or branched alkoxy having up to 5 carbon atoms, aryl or aralkoxy, each of which has up to 10 carbon atoms, and a 5- to 7-membered aromatic, optionally benzo-fused heterocycle having up to 3 heteroatoms from the group comprising S, N and/or O, it being possible for the rings in turn to be substituted by halogen, hydroxyl, cyano, linear or branched alkoxy having up to 6 carbon atoms, or a radical of the formula $(NH)_a-CONR^8R^9$,
wherein
$R^8$ and $R^9$ are identical or different and are hydrogen or linear or branched alkyl having up to 6 carbon atoms,
and
a is the number 0 or 1,
or
L is a radical of the formula $-(CH_2)_b-T-(CH_2)_c$,
wherein
b and c are identical or different and are the number 0, 1, 2, 3, 4 or 5,
and
T is cycloalkyl having 3 to 6 carbon atoms, aryl having 6 to 10 carbon atoms or a 3- to 8-membered, saturated or unsaturated, optionally benzo-fused and/or heterocyclically or carbocyclically bridged heterocycle having up to 3 heteroatoms from the group comprising S, N and/or O, wherein all the ring systems are optionally substituted by up to 3 identical or different substituents selected from halogen, cyano, hydroxyl, nitro, carbonyl, linear or branched alkyl, alkoxycarbonyl or alkoxy, each of which has up to 9 carbon atoms, and a radical of the formula $-CO-NR^{10}R^{11}$,
wherein
$R^{10}$ and $R^{11}$ are as defined above for $R^8$ and $R^9$ and are identical thereto or different therefrom, $R^1$ and $R^2$ are identical or different and are hydrogen, phenyl or linear or branched alkyl having up to 6 carbon atoms which is optionally substituted by hydroxyl, halogen or a radical of the formula $-NR^{12}R^{13}$,
wherein
$R^{12}$ and $R^{13}$ are identical or different and are as defined above for $R^8$ and $R^9$,
or
$R^1$, $R^2$ and L, together with the two nitrogen atoms, form a 5- to 8-membered, saturated, partially unsaturated or aromatic heterocycle which is optionally benzo-fused and/or substituted by hydroxyl, carboxyl, linear or branched acyl or alkoxycarbonyl, each of which has up to 6 carbon atoms, phenyl or linear or branched alkyl having up to 6 carbon atoms, which in turn is substituted by hydroxyl, carboxyl, ureido, linear or branched alkoxy, acylamino or alkoxycarbonyl, each of which has up to 5 carbon atoms, or a group of the formula $-(O)_d-(CO)_e-NR^{14}R^{15}$,
wherein
d is the number 0 or 1,
e is the number 0 or 1,
and
$R^{14}$ and $R^{15}$ are identical or different and are as defined above for $R^8$ and $R^9$,
and/or the heterocycle is optionally substituted by a radical of the formula $-(CO)_f-NR^{16}R^{17}$ or $-(O)_{d'}-(CO)_{e'}NR^{14'}R^{15'}$,
wherein
f is as defined above for e and is identical thereto or different therefrom, $R^{16}$ and $R^{17}$ are identical or different and are as defined above for $R^8$ and $R^9$,
and d', e', $R^{14'}$ and $R^{15'}$ are identical or different and are as defined above d, e, $R^{14}$ and $R^{15}$,
or, in the case where b is the number 0 and c is as defined above, or c is the number 0 and b is as defined above, T and $R^1$ or, respectively, T and $R^2$, in each case together with the nitrogen atom, form a 3- to 8-membered, optionally benzo-fused and/or heterocyclically or carbocyclically bridged, saturated heterocycle having up to 2 heteroatoms from the group comprising S, N and/or O,
and
$R^3$, $R^4$, $R^5$ and $R^6$ are identical or different and are hydrogen, phenyl or linear or branched alkyl having up to 8 carbon atoms which is optionally substituted by hydroxyl, halogen or a radical of the formula $-NR^{18}R^{19}$,
wherein
$R^{18}$ and $R^{19}$ are identical or different and are as defined above for $R^8$ and $R^9$,
or
$R^3$ and $R^4$ and/or $R^5$ and $R^6$, in each case together with the nitrogen atom, form a 5- to 7-membered saturated heterocycle which can optionally contain up to 2 further heteroatoms from the group comprising S and O, or a radical of the formula $-NR^{20}$,
wherein
$R^{20}$ is as defined above for $R^7$ and is identical thereto or different therefrom,
with the proviso that if $R^3$, $R^4$, $R^5$ and $R^6$ are hydrogen, $R^1$, $R^2$ and L, together with the two nitrogen atoms, must not be piperazinyl or 1,4-diazacycloheptyl,
and their salts.

Biocompatible salts are preferred within the framework of the present invention. Biocompatible salts of the novel 2,2'-bridged bis-2,4 -diaminoquinazolines can be salts of the substances according to the invention with mineral acids, carboxylic acids or sulphonic acids. Examples of particularly preferred salts are those with hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, propionic acid, lactic acid, tartaric acid, citric acid, fumaric acid, maleic acid or benzoic acid.

The compounds according to the invention can be present in different stereoisomeric forms within the framework of the present invention. The compounds according to the invention exist in stereoisomeric forms which either behave as image and mirror image (enantiomers) or do not behave as image and mirror image (diastereoisomers). The invention relates both to the antipodes and to the racemic forms and the diastereoisomeric mixtures. The racemic forms and the diastereoisomers can be resolved in known manner into the stereoisomerically pure components.

Within the framework of the invention, a heterocycle is generally a saturated or unsaturated 5- to 8-membered, preferably 6- or 7-membered heterocycle which can contain up to 3 heteroatoms from the group comprising S, N and/or O. Examples which may be mentioned are pyridyl, thienyl, furyl, pyrrolyl, thiazolyl, oxazolyl, imidazolyl, morpholinyl or piperidyl. Pyridyl and thienyl are preferred.

A 3- to 8-membered saturated heterocycle bonded via the nitrogen atom, which can also contain up to 2 oxygen, sulphur and/or nitrogen atoms as heteroatoms, is generally azetidinyl, piperidyl, morpholinyl, piperazinyl, 2,3,4,5-tetrahydro-1H-benzo-[1,43]diazepine, pyrrolidinyl, 1,4-diazacycloheptyl or [1,5]-diazocanyl. 7- and 8-membered rings with one oxygen atom and/or up to 2 nitrogen atoms, for example 1,4-diazacycloheptyl or [1,5]-diazoxanyl, are preferred. 1,4-Diazacycloheptyl, [1,5]-diazocanyl and 2,3,4,5-tetrahydro-1H-benzo-[1,4]diazepine are particularly preferred.

Preferred compounds of the general formula (I) are those in which

A, A', D, D', E and E' are identical or different and are hydrogen, fluorine, chlorine, bromine, hydroxyl, nitro, trifluoromethyl, trifluoromethoxy or linear or branched alkyl or alkoxy, each of which has up to 4 carbon atoms, L is a linear or branched alkylene chain having up to 15 carbon atoms which is optionally interrupted by an oxygen or sulphur atom or by a group of the formula —$NR^7$,
wherein $R^7$ is hydrogen or linear or branched alkyl having up to 3 carbon atoms, and where the alkylene chain is optionally substituted by up to 2 identical or different substituents selected from hydroxyl, linear or branched alkoxy having up to 4 carbon atoms, phenyl, benzyloxy, phenoxy, pyridyl, pyrimidyl, pyridazinyl, quinolyl and isoquinolyl, it being possible for the rings in turn to be substituted by fluorine, chlorine, bromine, hydroxyl, cyano, linear or branched alkoxy having up to 4 carbon atoms, or a radical of the formula —$(NH)_a$—$CONR^8R^9$,
wherein $R^8$ and $R^9$ are identical or different and are hydrogen or linear or branched alkyl having up to 4 carbon atoms,
and a is the number 0 or 1,
or a radical of the formula —$(CH_2)_b$—T—$(CH_2)_c$,
wherein b and c are identical or different and are the number 0, 1, 2, 3 or 4,
and T is cyclopropyl, cyclobutyl, cyclopentyl, cyclohexyl, cycloheptyl, phenyl, naphthyl, pyridyl, quinolyl, isoquinolyl, morpholinyl or piperidinyl which is optionally substituted by up to 2 identical or different substituents selected from fluorine, chlorine, bromine, cyano, hydroxyl, carboxyl, linear or branched alkyl, alkoxycarbonyl or alkoxy, each of which has up to 7 carbon atoms, and a radical of the formula —CO—$NH_2$, $R^1$ and $R^2$ are identical or different and are hydrogen or linear or branched alkyl having up to 3 carbon atoms which is optionally substituted by hydroxyl, fluorine or a radical of the formula —$NR^{12}R^{13}$,
wherein $R^{12}$ and $R^{13}$ are identical or different and are hydrogen or linear or branched alkyl having up to 5 carbon atoms,
or $R^1$, $R^2$ and L, together with the two nitrogen atoms, form a 2,3,4,5-tetrahydro-1H-benzo-[1,4]diazepine, piperazinyl, 1,4 -diazacycloheptyl or [1,5]-diazocanyl ring which is optionally substituted by hydroxyl, carboxyl, linear or branched acyl or alkoxycarbonyl, each of which has up to 5 carbon atoms, phenyl or linear or branched alkyl having up to 5 carbon atoms, which can in turn be substituted by hydroxyl, carboxyl, ureido, linear or branched alkoxy, acylamino or alkoxycarbonyl, each of which has up to 4 carbon atoms, or a group of the formula —$(O)_d$—$(CO)_e$—$NR^{14}R^{15}$,
wherein d is the number 0 or 1, e is the number 0 or 1,
and $R^{14}$ and $R^{15}$ are identical or different and are hydrogen or linear or branched alkyl having up to 4 carbon atoms, and/or the heterocycles are optionally substituted by a radical of the formula —$(CO)_f NR^{16}R^{17}$ or —$(O)_{d'}$—$(CO)_{e'}$—$NR^{14}R^{15}$,
wherein f is as defined above for e and is identical thereto or different therefrom, $R^{16}$ and $R^{17}$ are identical or different and are as defined above for $R^{14}$ and $R^{15}$,
and d', e', $R^{14}$ and $R^{15}$ are identical or different and are as defined above d, e, $R^{14}$ and $R^{15}$ or, in the case where b is the number 0 and c is as defined above, or c is the number 0 and b is as defined above, T and $R^1$ or, respectively, T and $R^2$, in each case together with the nitrogen atom, form a piperidine, morpholine, pyrrolidine or 4-azatricyclo[5.2.2.0]-2.6-undecenyl ring,
and $R^3$, $R^4$, $R^5$ and $R^6$ are identical or different and are hydrogen or linear or branched alkyl having up to 7 carbon atoms which is optionally substituted by hydroxyl, fluorine or a radical of the formula —$NR^{18}R^{19}$,
wherein $R^{18}$ and $R^{19}$ are identical or different and are as defined above for $R^{14}$ and $R^{15}$, or R³ and R⁴ and/or R⁵ and R⁶, in each case together with the nitrogen atom, form a morpholine, piperazinyl, piperidinyl or pyrrolidinyl ring, with the proviso that if R³, R⁴, R⁵ and R⁶ are hydrogen, R¹, R² and L, together with the two nitrogen atoms, must not be piperazinyl or 1,4-diazacycloheptyl, and their salts.

Particularly preferred compounds of the general formula (I) are those in which

A, A', D, D', E and E' are identical or different and are hydrogen, fluorine, chlorine, nitro,' trifluoromethyl, trifluoromethoxy or linear or branched alkyl having up to 3 carbon atoms, L is a linear or branched alkylene chain having up to 10 carbon atoms which is optionally interrupted by an oxygen or sulphur atom or by a group of the formula —NR⁷,
wherein
R⁷ is hydrogen or linear or branched alkyl having up to 3 carbon atoms,
and where the alkylene chain is optionally substituted by up to 2 identical or different substituents selected from hydroxyl, linear or branched alkoxy having up to 3 carbon atoms, phenyl, benzyloxy, phenoxy and pyridyl, it being possible for the rings in turn to be substituted by fluorine, chlorine, bromine, hydroxyl, cyano, linear or branched alkoxy having up to 3 carbon atoms, or a radical of the formula —(NR)ₐ—CONR⁸R⁹,
wherein
R⁸ and R⁹ are identical or different and are hydrogen or linear or branched alkyl having up to 3 carbon atoms,
and
a is the number 0 or 1,
or
L is a radical of the formula —(CH₂)ᵦ—T—(CH₂)ₑ,
wherein
b and c are identical or different and are the number 0, 1, 2, 3 or 4,
and
T is cyclopropyl, cyclobutyl, cyclopentyl, cyclohexyl, cycloheptyl, phenyl, pyridyl or piperidinyl which is optionally substituted by fluorine, chlorine, bromine, cyano, hydroxyl, carboxyl, linear or branched alkyl, alkoxycarbonyl or alkoxy, each of which has up to 5 carbon atoms, or a radical of the formula —CO—NH₂, R¹ and R² are identical or different and are hydrogen or linear or branched alkyl having up to 3 carbon atoms which is optionally substituted by hydroxyl, fluorine or a radical of the formula —NR¹²R¹³,
wherein
R¹² and R¹³ are identical or different and are hydrogen or linear or branched alkyl having up to 4 carbon atoms,
or R¹, R² and L, together with the two nitrogen atoms, form a 2,3,4,5-tetrahydro-1H-benzo-[1,4]diazepine, 1,4-diazacycloheptyl or [1,5]-diazoxanyl ring which is optionally substituted by hydroxyl, carboxyl, linear or branched acyl or alkoxycarbonyl, each of which has up to 4 carbon atoms, phenyl or linear or branched alkyl having up to 4 carbon atoms, which in turn can be substituted by hydroxyl, carboxyl, ureido, linear or branched alkoxy, acylamino or alkoxycarbonyl, each of which has up to 3 carbon atoms, or a group of the formula —(O)_d—(CO)_e—NR¹⁴R¹⁵,
wherein d is the number 0 or 1,
e is the number 0 or 1,
and
R¹⁴ and R¹⁵ are identical or different and are hydrogen or linear or branched alkyl having up to 3 carbon atoms, and/or the heterocycles are optionally substituted by a radical of the formula —(CO)_f—NR¹⁶R¹⁷ or —(O)_{d'}—(CO)_{e'}—NR¹⁴'R¹⁵',
wherein
f is as defined above for e and is identical thereto or different therefrom,
R¹⁶ and R¹⁷ are identical or different and are as defined above for R¹⁴ and R¹⁵,
and
d', e', R¹⁴' and R¹⁵' are identical or different and are as defined above d, e, R¹⁴ and R¹⁵
or, in the case where b is the number 0 and c is as defined above, or c is the number 0 and b is as defined above, T and R¹ or, respectively, T and R², in each case together with the nitrogen atom, form a piperidine, pyrrolidine or 4-azatricyclo[5.2.2.0]-2,6-undecenyl ring,
and R³, R⁴, R⁵ and R⁶ are identical or different and are hydrogen or linear or branched alkyl having up to 5 carbon atoms which is optionally substituted by hydroxyl, fluorine or a radical of the formula —NR¹⁸R¹⁹,
wherein
R¹⁸ and R¹⁹ are identical or different and are as defined above for R¹⁴ and R¹⁵,
or R³ and R⁴ and/or R⁵ and R⁶, in each case together with the nitrogen atom, form a morpholine, piperazinyl, piperidinyl or pyrrolidinyl ring, with the proviso that if R³, R⁴, R⁵ and R⁶ are hydrogen, R¹, R² and L, together with the two nitrogen atoms, must not be piperazinyl or 1,4-diazacycloheptyl, and their salts.

Processes for the preparation of the compounds of the general formula (I) according to the invention have also been found, said processes being characterized in that

[A] 2 equivalents of the compounds of the general formula (II):

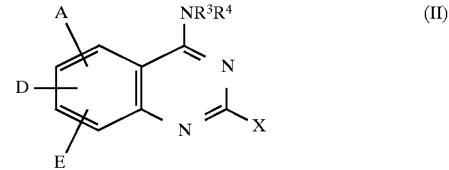

in which
A, D, E, R³ and R⁴ are as defined,
and
X is halogen, preferably chlorine, are reacted with diamines of the general formula (III):

in which
R¹, R² and L are as defined above,
optionally in inert solvents and optionally in the presence of a base and/or an iodine salt,
or

[B] 1 equivalent of the compound of the general formula (II) is reacted with the compounds of the general formula (III), under the conditions of process [A], to give compounds of the general formula (IV):

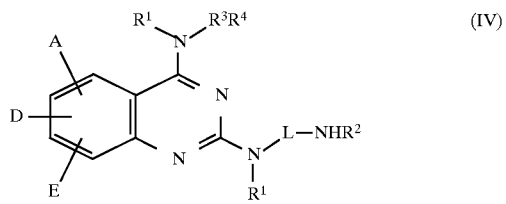

and these are then reacted with compounds of the general formula (IIa):

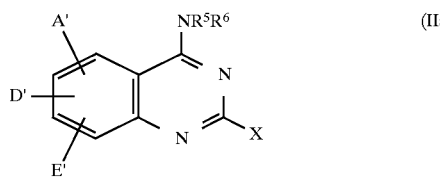

in which
A', D', E', $R^5$, $R^6$ and X are as defined.

The process according to the invention can be exemplified by the following equation:

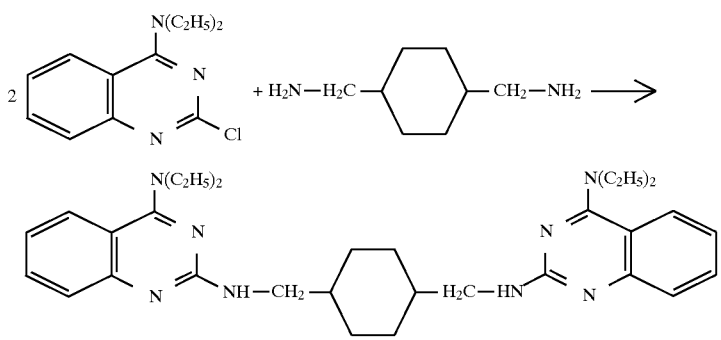

Suitable solvents are the conventional solvents which are not affected by the reaction conditions. These preferably include alcohols such as methanol, ethanol, propanol, isopropanol, hexanol, octanol or phenol, ethers such as diethyl ether, dioxane, tetrahydrofuran, glycol dimethyl ether or butyl methyl ether, ketones such as acetone or butanone, amides such as N-methylpyrrolidone, dimethylformamide or N-methylphosphorotriamide, dimethyl sulphoxide, acetonitrile, butyronitrile, ethyl acetate, halogenated hydrocarbons such as methylene chloride, chloroform or carbon tetrachloride, pyridine, picoline or N-methylpiperidine. It is also possible to use mixtures of said solvents. Tetrahydrofuran, butyronitrile, phenol and N-methylpyrrolidone are preferred. The reaction can also be carried out without a solvent. Suitable bases are the conventional inorganic or organic bases. These preferably include alkali metal carbonates such as sodium or potassium carbonate, or organic amines such as diethylamine, triethylamine, tripropylamine, pyridine, picoline, N-methylpiperidine, lutidine or diisopropylethylamine. Diisopropylethylamine and tripropylamine are preferred.

Suitable iodine salts are alkali metal iodides such as lithium iodide, sodium iodide, potassium iodide and caesium iodide, and tetralkylammonium iodides such as benzyltributylammonium iodide. It is preferable to use sodium iodide and potassium iodide.

The iodine salts are generally used in an amount of 0.001 to 1 mol, based on 1 mol of the compounds of the general formula (II).

The base is used here in an amount of 1 to 5 mol, preferably of 1 to 2 mol, based on 1 mol of the compounds of the general formula (II).

The reactions are generally carried out in the temperature range between $-20°$ C. and the reflux temperature of the solvent, preferably between $+20°$ C. and the reflux temperature of the solvent.

The reaction can be carried out at normal, elevated or reduced pressure (e.g. 0.5 to 5 bar). It is generally carried out at normal pressure.

Some of the compounds of the general formula (II) are known or they can be prepared by known methods, for example by reacting the corresponding 2,4-dichloroquinazolines with diethylamine.

The compounds of the general formula (III) are known per se or can be prepared by conventional methods.

Some of the compounds of the general formulae (IV) and (IVa) are known or novel and they can be prepared as described above.

The compounds according to the invention possess a valuable pharmacological spectrum of action which could not be anticipated.

The compounds according to the invention are ligands for apamin-sensitive potassium channels. This can be shown by studying the affinity for apamine binding sites, e.g. in bovine cerebral membranes. The compounds according to the invention inhibit the ion flows through these channels, as can be shown by rubidium efflux experiments and with electrophysiological methods.

The compounds have a positive influence on learning and memory faculties, as demonstrated by their performance-enhancing action in typical learning and memory models like the water maze, the Morris maze, passive avoidance or reminiscence tests in automated Skinner boxes. They possess an antidepressant potential, as verified by their activity in the Porsolt rat swimming test.

The compounds according to the invention are also suitable for the treatment of myotonic dystrophy, alcoholism and other addiction diseases, sleep disturbances and bronchial asthma.

By virtue of their pharmacological properties, the compounds according to the invention can be used for the preparation of drugs for the treatment of degenerative diseases of the central nervous system, e.g. those occurring in cases of dementia (multi-infarct dementia, MID, primary degenerative dementia, PDD, presenile Alzheimer's disease, HIV dementia and other forms of dementia).

They are also suitable for the treatment of age-related cerebral faculty impairment, organic brain syndrome (OBS) and age-associated memory impairment (AAMI).

They are suitable for the treatment of depression.

1) Binding of $^{125}$I-apamin to bovine cerebral membrane

Calf brains were obtained from the local abattoir. The hippocampus was prepared on ice and a membrane suspension was made up by homogenization twice in buffer (100 mM Tris-HCl, KCl 5 mM, pH 7.4) and centrifugation at 43,000×g. In a total volume of 500 μl, the incubation mixture contained 200 μg of membrane protein, 30 pM $^{125}$I-apamine and test substances in the concentration range $1\times10^{-9}$ to $1\times10^{4}$M. The non-specific binding of $^{125}$I-apamin was determined in the presence of $1\times10^{-7}$M unlabelled apamin.

After preincubation for 30 min at room temperature (test substances and membrane homogenate), the samples were placed on ice for 10 min before the radioligand was added. The main incubation time was 60 min on ice. When the reaction time had elapsed, an excess of ice-cooled incubation buffer was added to each sample and the mixture was filtered with suction through cellulose acetate/nitrate membrane filters. The amount of bound $^{125}$I-apamin was measured with a gamma counter.

TABLE A

| Ex. No. | $K_i$ (nmol/l) |
| --- | --- |
| 1 | 340 |
| 4 | 140 |

2) Non-radioactive $Rb^+$ efflux assay for the identification of potassium channel modulators The potassium in PC12 cells is exchanged with rubidium, which is not present in the cells. This exchange is performed by incubating the cells over a period of 4 h in a physiological buffer containing 5.4 mM RbCl without KCl. This rubidium subsequently serves as a tracer for potassium.

The cells laden with $Rb^+$ in this way are washed three times and then stimulated by depolarization with 50 mM KCl to open potassium channels (10 min), causing $Rb^+$ to flow out of the cells into the supernatant according to the concentration gradient. The rubidium contents in the cell supernatant and in the residual cells after they have been lysed with 1% Triton X-100 are then determined by means of atomic absorption spectroscopy. The relative proportion of rubidium in the cell supernatant (=$Rb^+$ efflux) is used as a measure of the potassium channel activity.

The effect of substances on the channel activity is measured by co-incubating the test substance over the ten-minute stimulation period and determining its effect on the $Rb^+$ efflux in the manner described above.

TABLE B

| Compound | % inhibition of the Rb efflux at a test concentration of 10 μM |
| --- | --- |
| 2 | 72 |
| 3 | 63 |

3) Morris maze

Male ICR mice, 6–8 wks old and approx. 22–28 g, were obtained from Harlan Sprague-Dawley, Inc. (Indianapolis, Ind.) and housed 8/cage with ad libitum access to food and water.

The behavioral apparatus consisted of a circular galvanized steel tank painted white with a diameter of 76 cm and divided into four equally spaced quadrants, each containing a plastic fitting that allowed for the placement of an escape platform. Prior to the start of the behavioral testing, the maze was filled daily to a depth of 1 cm above the escape platform (25 cm deep), maintained at a temperature of approx. 22° C., and was made opaque by the addition of 0.9 kg of powdered milk. Numerous stationary visual cues were present in the testing room. The data were recorded with the Multiple Zone Distance Traveled program of the Video-V analysis system (Columbus Instruments International Corp., Columbus, Ohio).

After a 1 week acclimatization to the animal facility, the mice were given a 90 sec free swim, during which no escape platform was present. One to three days later, acquisition training began and consisted of 4 trials on each day for a total of three days (12 total trials), during which no drugs were given. The mice were randomly assigned a goal quadrant in which the escape platform was located. Animals were then placed in the maze (facing away from the center) at one of four equally spaced positions around the perimeter of the maze. The starting position varied for each mouse until they had started from each of the four positions once daily. On each of the training trials, the mice were allowed 120 sec to find the goal platform. If they failed to do so within the allotted time, they were placed on the platform. The intertrial interval was 30 sec, during which time the mouse remained on the platform. On the fourth day, the mice were given a single 30 sec probe trial in which no escape platform was present. Thirty min or 1 hr prior to the start of the probe trial, mice were randomly assigned to groups that were given either drug or vehicle, and the time spent in each quadrant was measured.

The present invention also includes pharmaceutical formulations which contain one or more compounds of the general formula (I) together with inert, non-toxic, pharmaceutically appropriate adjuncts and excipients, or which consist of one or more active substances of the formula (I), as well as processes for the preparation of these formulations.

The active substances of the formula (I) should be present in these formulations in a concentration of 0.1 to 99.5% by weight, preferably of 0.5 to 95% by weight of the total mixture.

In addition to the active substances of the formula (I), the pharmaceutical formulations can also contain other pharmaceutical active substances. The pharmaceutical formulations mentioned above can be prepared in conventional manner by known methods, for example with one or more adjuncts or excipients.

To achieve the desired result, it has generally proved advantageous to administer the active substance or substances of the formula (I) in total amounts of about 0.01 to about 100 mg/kg, preferably in total amounts of about 0.01 mg/kg to 10 mg/kg of body weight per 24 hours, optionally in the form of several individual doses.

However, it may be advantageous to deviate from said amounts, depending on the nature and body weight of the subject treated, the individual response to the drug, the nature and severity of the disease, the type of formulation and administration and the time or interval at which the drug is administered.

Starting Compounds

EXAMPLE I
2-Chloro-4-diethylaminoquinazoline

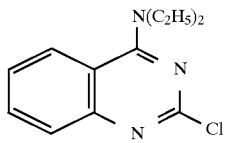

10.4 ml of diethylamine in 10 ml of diethyl ether were added dropwise to a solution of 10.0 g of 2,4-dichloroquinazoline in 400 ml of diethyl ether and the mixture was stirred for 3 h at room temperature. After distillation of the solvent under vacuum, the residue was taken up with 200 ml of methanol and stirred with 10 g of basic ion exchanger (Lewatit M600) for 3 h. The ion exchanger was filtered off and the filtrate was concentrated to dryness on a rotary evaporator. The residue was taken up with 200 ml of dichloromethane and the solution was washed twice with 50 ml of water. After the organic phase had been dried over magnesium sulphate and the solvent stripped off, the crude product was treated with 50 ml of diethyl ether/petroleum ether (1/1) and left to crystallize at 4° C. overnight.
Yield: 9.12 g (77%)
M.p.: 76° C.
4-(1-Pyrrolidino)-2-chloroquinazoline was obtained by the same method with pyrrolidine.
The 2,4-dichloroquinazoline used as educt was prepared by known processes [Eur. J. Med. Chem. 12, 1977, 325].
2,6-Dichloro-4-diethylaminoquinazoline was prepared from 2,4,6-trichloroquinazoline by the process indicated above.

EXAMPLE II
2,6-Bis-(aminomethyl)-pyridine

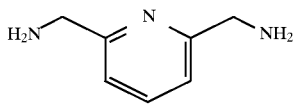

A mixture of 2,6-bis-(hydroxymethyl)-pyridine (556 mg, 4.0 mmol) and triphenylphosphine (1.05 g, 8.0 mmol) was dissolved in THF (20 ml) and cooled to 0° C. Phthalimide (1.2 g, 8.0 mmol) was added and diethyl azodicarboxylate (1.2 ml, 8.0 mmol) was then added dropwise. The cooling bath was removed and the mixture was stirred at RT overnight. It was concentrated on a rotary evaporator and the residue was purified by chromatography on silica gel (eluent: methylene chloride/ethanol, 100/2) to give 2,6-bis-(phthalimidomethyl)-pyridine in the form of a solid.
M.p.: >250° C.
Yield: 1.11 g (70%)
Hydrazine hydrate (2.4 ml, 50 mmol) was added to a solution of 2,6-bis-(phthalimidomethyl)-pyridine (1.99 g, 5.0 mmol) in 95% ethanol (50 ml). The mixture was refluxed for 3 hours. After cooling it was concentrated on a rotary evaporator and the residue was purified by chromatography on silica gel (eluent: methylene chloride/ethanol, 100/2) to give 2,6-bis-(aminomethyl)-pyridine in the form of a yellow oil.
Yield: 690 mg (100%)
NMR (200 MHz, $d_6$-DMSO): $\delta$=7.68 (t, 1H, J=9.0 Hz); 7.26 (d, 2H, J=9.0 Hz) and 3.78 (s, 4H)

EXAMPLE III
Methyl 1,4-dibenzyl-[1,4]-diazepan-6-carboxylate

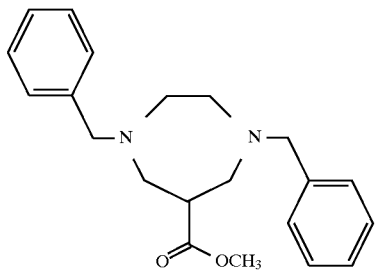

A solution of 8.8 g (34 mmol) of methyl 3-bromo-2-bromomethylpropionate in 80 ml of absolute toluene is added dropwise at room temperature, with stirring, to a solution of 8.0 g (33 mmol) of N,N'-dibenzyl-ethane-1,2-diamine and 6.7 g (66 mmol) of triethylamine in 60 ml of absolute toluene and the mixture is then stirred for 16 hours at 80°–90° C. After cooling, it is shaken with 20 ml of aqueous sodium carbonate solution and the organic phase is separated off and dried over sodium sulphate. 11 g of a yellow oil are isolated from the toluene solution and this is purified by column chromatography on silica gel (methylene chloride/methanol, 100/2) to give methyl 1,4-dibenzyl-[1,4]-diazepan-6-carboxylate in the form of a light yellow oil.
Yield: 6.0 g (53%)
$R_f$ (silica gel; methylene chloride/methanol, 100/2): 0.23

EXAMPLE IV
1,4-Dibenzyl-[1,4]-diazepan-6-carboxamide

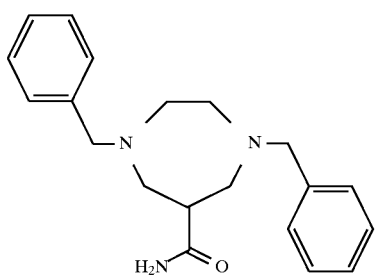

Anhydrous ammonia is introduced up to the saturation point, with ice-cooling at 0°–5° C., into a solution of 6.0 g (18 mmol) of the compound of Example III in 20 ml of absolute methanol, to which 0.1 g of potassium cyanide has been added. After the mixture has been standing for 14 days at room temperature, the solvent is evaporated off and the colorless residue is chromatographed on silica gel (methylene chloride/methanol, 100/2) to give the amide in the form of colorless crystals.
Yield: 5.0 g (87%)
M.p.: 76°–77° C.
1,4-Dibenzyl-[1,4]-diazepan-6-carboxamide dihydrochioride:
0.36 g (95%) of the abovementioned compound from 0.31 g (0.96 mmol) of the free base by the addition of HCl/diethyl ether; colorless crystals.
M.p.: 215° C.

EXAMPLE V

[1,4]-Diazepan-6-carboxamide

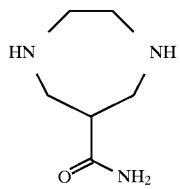

4.3 g (13 mmol) of 1,4-dibenzyl-[1,4]-diazepan-6-carboxamide are dissolved in 100 ml of methanol and hydrogenated at room temperature and normal pressure for 2.5 hours in the presence of 0.4 g of 10% palladium on activated charcoal. The mixture is filtered on kieselguhr and the filtrate is evaporated to dryness. Treatment of the residue with cyclohexane gives the carboxamide in the form of colorless crystals.

Yield: 1.88 g (99%)
M.p.: 178°–179° C.

Preparatory Examples

EXAMPLE 1

1,5-Bis-(4-diethylaminoquinazolin-2-yl)-[1,5]-diazoxane

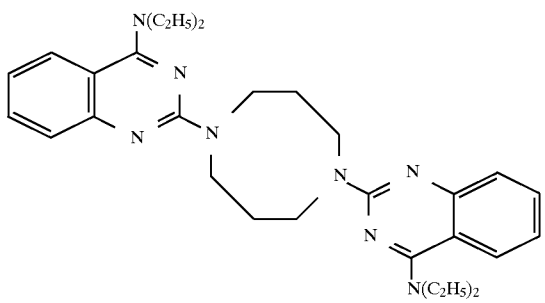

25 mg of potassium iodide are added to 2.06 g (8.8 mmol) of 2-chloro-4-diethylamino-quinazoline, 0.5 g (4.4 mmol) of [1,5]-diazocane and 0.206 g (2.0 mmol) of phenol and the mixture is heated at 140° C. for 1.5 hours. After cooling, the crude product, a vitreous solid, is dissolved in methanol, the solution is evaporated to dryness and the residue is taken up with methylene chloride and subjected to preliminary purification by chromatography on silica gel with methylene chloride/methanol, 100/1 to 100/5. The eluates are evaporated to give 2.0 g of product, which is dissolved in methylene chloride, shaken with sodium hydroxide solution and washed with water until the washings are neutral. The organic phase is dried and the solvent is evaporated off to give 1.44 g of product, which is chromatographed twice on silica gel. Eluent: methylene chloride/methanol/conc. aqueous ammonia solution, (1) 100/4/0.4; (2) 100/2/0.2. The eluates are evaporated to isolate 0.99 g of product, which is crystallized from ethyl acetate.

M.p.: 128° C.
Yield: 0.65 g (29%)

EXAMPLE 2

$N^2$-[4-(4-Diethylamino-quinazolin-2-yl)-4-aza-tricyclo[5.2.2.0$^{2,6}$]undec-8-en-1-yl-methyl]-$N^4$,$N^4$-diethyl-quinazoline-2,4-diamine dihydrochloride

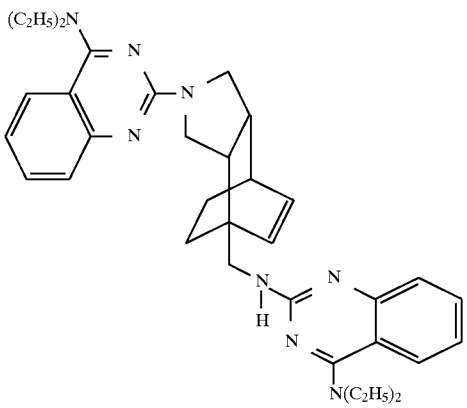

A mixture of 1.32 g (5.6 mmol) of 2-chloro-4-diethylamino-quinazoline, 0.5 g (2.8 mmol) of C-(4-aza-tricyclo[5.2.2.0$^{2,6}$]undec-8-en-1-yl)-methylamine, 0.132 g (1.4 mmol) of phenol and 16 mg of potassium iodide is reacted for 1 hour at 140° C. under argon. After cooling, the solidified melt is dissolved in methanol, HCl/diethyl ether is added and the mixture is evaporated to dryness. The residue is taken up with methylene chloride and purified by chromatography on silica gel (eluent: methylene chloride/methanol, 100/1) to give the free base in amorphous form after treatment with sodium hydroxide solution.

Yield: 0.94 g (58%)

0.93 g of base is dissolved in methylene chloride and treated with 2 equivalents of HCl/diethyl ether. The crystalline dihydrochloride is obtained by evaporation of the solvent and the addition of diethyl ether.

M.p.: 186° C.
Yield: 0.88 g (85%)

EXAMPLE 3

1,4-Bis-(4-diethylamino-2-quinazolyl)-1,4-diazacycloheptane

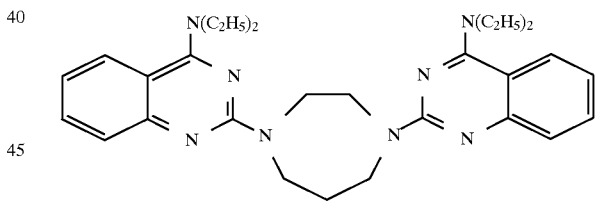

3.06 g of 2-chloro-4-diethylaminoquinazoline and 650 mg of 1,4-diazacycloheptane were suspended in 65 ml of butonitrile, and 2.26 ml of diisopropylethylamine were added. After refluxing for 16 hours and cooling to room temperature, the solution was treated with 50 ml of 1N sodium hydroxide solution and 100 ml of dichloromethane. The organic phase was washed with water until the washing were neutral, dried over magnesium sulphate and concentrated to dryness. The crude product could be purified by extraction of the residue by stirring with tert-butyl methyl ether.

Yield: 1.13 g (35%)

$^1$H NMR (CDCl$_3$, 400 MHz): 1.36 (t, 12H, CH$_2$C$\underline{H}_3$), 2.15 (quintuplet, 2H, CH$_2$), 3.62 (q, 8H, C$\underline{H}_2$CH$_3$), 3.77 (t, 4H, 2CH$_2$—N), 4.08 (s, 4H, 2CH$_2$—N), 6.98 (m, 2H, Ar-H), 7.46 (m, 4H, Ar-H), 7.72 (d, 2H, Ar-H)

EXAMPLE 4

1,4-Bis-(6-chloro-4-diethylamino-2-quinazolyl)-1,4-diazacycloheptane

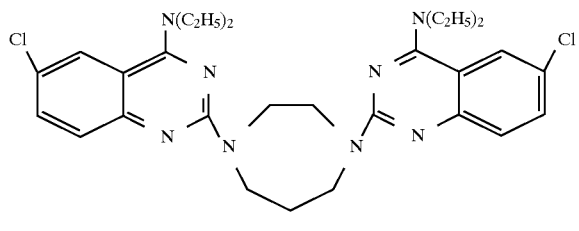

400 mg of 4,6-dichloro-2-diethylaminoquinazoline, 75 mg of 1,4-diazacycloheptane, 10 ml of butyronitrile and 0.26 ml of diisopropylethylamine.
Yield: 200 mg (47%)

EXAMPLE 5
2,6-Bis-(N',N"-(N-diethylaminoquinazolin-2-yl) aminomethyl)-pyridine

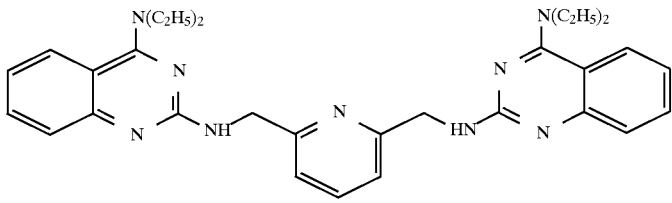

A mixture of 2,6-bis-(aminomethyl)-pyridine (Example II) (400 mg 2.9 mmol), 2-chloro-4-diethylaminoquinazoline (1.37 g, 5.8 mmol), phenol (200 mg, 2.1 mmol) and sodium iodide (6 ma 0.04 mmol) was reacted for 2 hours at 140° C. After cooling the residue was purified by chromatography on silica gel (eluent: methylene chloride/ethanol/ammonia, 100/10/1) to give the free base in the form of a solid.
M.p.: 147C.
Yield: 275 mg (18%)

The compounds listed in Table 1 are prepared analogously to the instructions in Example 5:

TABLE 1

| Ex. No. | -Z- | MS/m.p. (°C.) |
|---|---|---|
| 6 | 2,6-pyridinediyl | 536/147 |
| 7 | 2,5-pyridinediyl | 536/206 |
| 8 | 3,5-pyridinediyl | 536 |

TABLE 1-continued

| Ex. No. | -Z- | MS/m.p. (°C.) |
|---|---|---|
| 9 | 2,4-pyridinediyl | 536/105 |

General instructions for the synthesis of bis-[N-(2-quinazolyl)]-diamines 20 mmol of 2-chloroquinazoline derivative and 5 mmol of diamine were dissolved in 50 ml of acetonitrile, and 20 mmol of triethylamine were added. After fluxing for 80 hours, the solution was concentrated to dryness on a rotary evaporator and the residue was chromatographed on silica gel 60 (Merck 63–200 μm) using dichloromethane/methanol/acetic acid, 60/40/2.5 as the eluent. The product fractions were dissolved in 50 ml of methanol and stirred with 3 g of basic ion exchanger (Lewatit M600) for 2 h. The ion exchanger was then filtered off with suction and washed several times with methanol. After concentration of the filtrate to dryness, the last impurities were washed out of the residue with diethyl ether.

Yields: 25–50%

The compounds listed in Tables 2–6 are obtainable by this process.

TABLE 2

| Ex. No. | -Z- | $R_i$ value ($CH_2Cl_2$/MeOH/conc. $NH_3$) |
|---|---|---|
| 10 | $-NH(CH_2)_2-NH-$ | 0.70 (15/2/0.2) |
| 11 | $-NH(CH_2)_3-NH-$ | 0.61 (15/4/0.5) |
| 12 | $-NH(CH_2)_6-NH-$ | 0.66 (15/4/0.5) |

TABLE 2-continued

[Structure: bis(N-propylamino)benzamidine type with -Z- linker]

| Ex. No. | -Z- | $R_i$ value ($CH_2Cl_2$/MeOH/conc. $NH_3$) |
|---|---|---|
| 13 | [N-methyl, ortho-xylylenediamine derivative] | 0.54 (15/4/0.5) |
| 14 | [N-methyl, meta-xylylenediamine derivative] | 0.38 (15/4/0.5) |

TABLE 3

[Structure: bis[(2-diethylamino)ethylamino]benzamidine type with -Z- linker]

| Ex. No. | -Z- | $R_i$ value ($CH_2Cl_2$/MeOH/conc. $NH_3$) |
|---|---|---|
| 15 | $-NH(CH_2)_2NH-$ | 0.48 (15/2/0.2) |
| 16 | $-NH(CH_2)_3NH-$ | 0.74 (15/4/0.5) |
| 17 | $-NH(CH_2)_4NH-$ | 0.69 (15/6/0.6) |
| 18 | $-NH(CH_2)_6NH-$ | 0.60 (15/4/0.5) |
| 19 | [trans-1,2-cyclohexanediamine N,N'-dimethyl derivative] | 0.59 (15/4/0.5) |
| 20 | [1,4-cyclohexanediamine N,N'-dimethyl derivative] | 0.61 (15/4/0.5) |
| 21 | [meta-xylylenediamine N,N'-dimethyl derivative] | 0.60 (15/5/0.5) |
| 22 | [para-xylylenediamine N,N'-dimethyl derivative] | 0.64 (15/4/0.5) |

TABLE 4

[Structure: bis(N,N-diethylamino)benzamidine type with -Z- linker]

| Ex. No. | -Z- | $R_i$ value ($CH_2Cl_2$/MeOH/conc. $NH_3$) |
|---|---|---|
| 31 | $-NH(CH_2)_2NH-$ | 0.70 (50/10/1) |
| 32 | $-NH(CH_2)_3NH-$ | 0.23 (100/10/1) |
| 33 | $-NH(CH_2)_4NH-$ | 0.58 (50/10/1) |
| 34 | $-NH(CH_2)_5NH-$ | 0.63 (50/10/1) |
| 35 | $-NH(CH_2)_8NH-$ | 0.65 (50/10/1) |
| 36 | $-NH(CH_2)_9NH-$ | 0.87 (50/10/1) |
| 37 | $-NH(CH_2)_{10}NH-$ | 0.63 (100/10/1) |
| 38 | [para-xylylenediamine N,N'-dimethyl derivative] | 0.44 (100/10/1) |

TABLE 5

[Structure: bis(N,N-diethylamino)benzamidine type with -Z- linker]

| Ex. No. | -Z- | $R_i$ value ($CH_2Cl_2$/MeOH/conc. $NH_3$) |
|---|---|---|
| 31 | $-NH(CH_2)_2NH-$ | 0.70 (50/10/1) |
| 32 | $-NH(CH_2)_3NH-$ | 0.23 (100/10/1) |
| 33 | $-NH(CH_2)_4NH-$ | 0.58 (50/10/1) |
| 34 | $-NH(CH_2)_5NH-$ | 0.63 (50/10/1) |
| 35 | $-NH(CH_2)_8NH-$ | 0.65 (50/10/1) |
| 36 | $-NH(CH_2)_9NH-$ | 0.87 (50/10/1) |
| 37 | $-NH(CH_2)_{10}NH-$ | 0.63 (100/10/1) |
| 38 | [para-xylylenediamine N,N'-dimethyl derivative] | 0.44 (100/10/1) |

TABLE 6

[Structure: benzamidine derivative with $R^{23}R^{24}N-(CH_2)_n-NH-$ substituents and -Z- linker]

| Ex. No. | -Z- | $R^{23}R^{24}$ | n |
|---|---|---|---|
| 39 | $-NH-(CH_2)_6-NH-$ | $CH_3/CH_3$ | 1 |
| 40 | $-NH-(CH_2)_3-NH-$ | $CH_3/CH_3$ | 1 |

TABLE 6-continued

| Ex. No. | -Z- | $R^{23}R^{24}$ | n |
|---|---|---|---|
| 41 | $-NH-(CH_2)_6-NH-$ | $CH_3/CH_3$ | 2 |
| 42 | $-NH-(CH_2)_6-NH-$ | $C_2H_5/C_2H_5$ | 2 |

TABLE 7

| Ex. No. | -Z- | m.p./$R_f$ |
|---|---|---|
| 43 | $-NH-CH_2-CH_2-CH(CH_3)-CH_2-CH_2-NH-$ | 225° C. (A) |
| 44 | $-NH-CH_2-CH_2-CHOH-CH_2-CH_2-NH-$ | 140–143° C. (B) |
| 45 | $-NH-CH_2-CHOH-CH_2-NH-$ | oil (D) |
| 46 | $-NH-CH_2-CH(OCH_3)-CH_2-NH-$ | oil (E) |
| 47 | $-NH-CH_2-CH(OC_6H_5)-CH_2-NH-$ | oil, 0.73 (F) |
| 48 | $-NH-CH_2-C(CH_3)(OCH_2C_6H_5)-CH_2-NH-$ | oil (G) |
| 49 | (cyclohexane-1,3-diyl-bis(methylene-NH-)) | oil, 0.31 (H) |
| 50 | (1-methylpiperidin-4-yl-methyl-NH-) | 85° C. |
| 51 | (1-methylpiperidin-4-yl-NH-) | >245° C. (A) |
| 52 | (2,2'-(4-methyl-1,4-diazepane-1,4-diyl)... carboxamide) | 165° C. |

TABLE 7-continued

| Ex. No. | -Z- | m.p./R_f |
|---|---|---|
| 53 | [diazocane ring with -CH2OH substituent] | 123–124° C. (I) |
| 54 | [diazocane ring fused via o-xylylene] | 183–186° C. |
| 55 | [diazocane ring with -CO-N(C2H5)2 substituent] | 0.50 (K) |
| 56 | [diazocane ring with -OH substituent] | 174° C. |
| 57 | [diazocane ring with -N(C2H5)2 substituent] | 0.43 (K) |
| 58 | [diazocane ring with -OCO-NHC2H5 substituent] | 0.74 (K) |

(A) HCl salt
(B) HCl salt; recrystallized from 2-propanol/diisopropyl ether
(D) MS (DCl; NH$_3$): 489(M$^+$ + H), 259, 217
(E) MS (DCl; NH$_3$): 503 (M$^+$ + H), 470
(F) CH$_2$Cl$_2$/ethanol/conc. ammonia, 100/10/1
(G) MS (DCl; NH$_3$): 593 (M$^+$ + H)
(H) CH$_2$Cl$_2$/CH$_3$OH/NEt$_3$, 80/2/1
(I) Starting material H—Z—H prepared from Bn—Z—Bn by hydrogenation; Bn—Z—Bn obtainable from Example III by reduction
(K) Silica gel, eluent = CH$_2$Cl$_2$/MeOH/conc. NH$_3$, 100/10/1

We claim:
1. 2,2'-Bridged bis-2,4-diaminoquinazolines of the general formula (I):

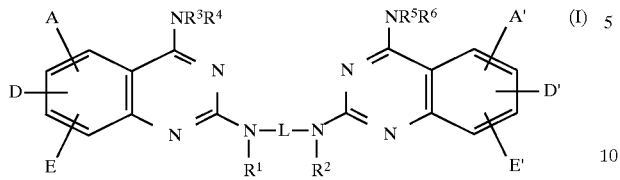

in which
A, A', D, D', E and E' are identical or different and are hydrogen, halogen, hydroxyl, nitro, trifluoromethyl, trifluoromethoxy or linear or branched alkyl or alkoxy, each of which has up to 6 carbon atoms,
L is a linear or branched alkylene chain having up to 20 carbon atoms which is optionally interrupted by an oxygen or sulphur atom or by a group of the formula —$NR^7$,
wherein
$R^7$ is hydrogen or linear or branched alkyl having up to 4 carbon atoms,
and where the alkylene chain is optionally substituted by up to 3 identical or different substituents selected from hydroxyl, linear or branched alkoxy having up to 5 carbon atoms, aryl or aralkoxy, each of which has up to 10 carbon atoms, and a 5- to 7-membered aromatic, optionally benzo-fused heterocycle having up to 3 heteroatoms from the group comprising S, N and/or O, it being possible for the rings in turn to be substituted by halogen, hydroxyl, cyano, linear or branched alkoxy having up to 6 carbon atoms, or a radical of the formula —$(NH)_a$—$CONR^8R^9$,
wherein
$R^8$ and $R^9$ are identical or different and are hydrogen or linear or branched alkyl having up to 6 carbon atoms,
and
a is the number 0 or 1,
and
$R^1$ and $R^2$ are identical or different and are hydrogen, phenyl or linear or branched alkyl having up to 6 carbon atoms enrich is optionally substituted by hydroxyl, halogen or a radical of the formula —$NR^{12}R^{13}$,
wherein
$R^{12}$ and $R^{13}$ are identical or different and are as defined above for $R^8$ and $R^9$,
or
$R^1$, $R^2$ and L, together with the two nitrogen atoms, form a 5- to 8-membered, saturated, partially unsaturated or aromatic heterocycle which is optionally benzo-fused and/or substituted by hydroxyl, carbonyl, linear or branched acyl or alkoxycarbonyl, each of which has up to 6 carbon atoms, phenyl or linear or branched alkyl having up to 6 carbon atoms, which in turn is substituted by hydroxyl, carbon?l, ureido, linear or branched alkoxy, acylamino or alkoxycarbonyl, each of which has up to 5 carbon atoms, or a group of the formula —$(O)_d(CO)_eNR^{14}R^{15}$,
wherein
d is the number 0 or 1,
e is the number 0 or 1,
and
$R^{14}$ and $R^{15}$ are identical or different and are as defined above for $R^8$ and $R^9$,
and/or the heterocycle is optionally substituted by a radical of the formula —$(CO)_f$—$NR^{16}R^{17}$ or —$(O)_{d'}$—$(CO)_{e'}$—$NR^{14'}R^{15'}$,
wherein
f is as defined above for e and is identical thereto or different therefrom,
$R^{16}$ and $R^{17}$ are identical or different and are as defined above for $R^8$ and $R^9$,
and
d', e', $R^{14'}$ and $R^{15'}$ are identical or different and are as defined above d, e, $R^{14}$ and $R^{15}$
and
$R^3$, $R^4$, $R^5$ and $R^6$ are identical or different and are hydrogen, phenyl or linear or branched alkyl having up to 8 carbon atoms which is optionally substituted by hydroxyl, halogen or a radical of the formula —$NR^{18}R^{19}$,
wherein
$R^{18}$ and $R^{19}$ are identical or different and are as defined above for $R^8$ and $R^9$,
or
$R^3$ and $R^4$ and/or $R^5$ and $R^6$, in each case together with the nitrogen atom, form a 5- to 7-membered saturated heterocycle which can optionally contain up to 2 further heteroatoms from the group comprising S and O, or a radical of the formula —$NR^{20}$,
wherein
$R^{20}$ is as defined above for $R^7$ and is identical thereto or different therefrom,
with the proviso that if $R^3$, $R^4$, $R^5$ and $R^6$ are hydrogen, $R^1$, $R^2$ and L, together with the two nitrogen atoms, must not be piperazinyl or 1,4-diazacycloheptyl,
provided that if $R^1$, $R^2$ and L together with the 2 nitrogen atoms are a piperazinyl radical, A, A', D, D', E and E' are not hydrogen or alkoxy
and their salts.
2. 2,2'-Bridged bis-2,4-diaminoquinazolines of the formula according to claim 1 in which
A, A', D, D', E and E' are identical or different and are hydrogen, fluorine, chlorine, bromine, hydroxyl, nitro, trifluoromethyl, trifluoromethoxy or linear or branched alkyl or alkoxy, each of which has up to 4 carbon atoms,
L is a linear or branched alkylene chain having up to 15 carbon atoms which is optionally interrupted by an oxygen or sulphur atom or by a group of the formula —$NR^7$,
wherein
$R^7$ is hydrogen or linear or branched alkyl having up to 3 carbon atoms,
and where the alkylene chain is optionally substituted by up to 2 identical or different substituents selected from hydroxyl, linear or branched alkoxy having up to 4 carbon atoms, phenyl, benzyloxy, phenoxy, pyridyl, pyrimidyl, pryidazinyl, quinolyl and isoquinolyl, it being possible for the rings in turn to be substituted by fluorine, chlorine, bromine, hydroxyl, cyano, linear or branched alkoxy having up to 4 carbon atoms, or a radical of the formula —$(NH)_a$—$CONR^8R^9$,
wherein
$R^8$ and $R^9$ are identical or different and are hydrogen or linear or branched alkyl having up to 4 carbon atoms,
and
a is the number 0 or 1,
$R^1$ and $R^2$ are identical or different and are hydrogen or linear or branched alkyl having up to 3 carbon atoms which is optionally substituted by hydroxyl, fluorine or a radical of the formula —$NR^{12}R^{13}$,
wherein
$R^{12}$ and $R^{13}$ are identical or different and are hydrogen or linear or branched alkyl having up to 5 carbon atoms, or R$^1$, R$^2$ and L, together with the two nitrogen atoms, form a piperazinyl, 2,3,4,5-tetrahydro-1H-benzo-[1,4]diazepine, 1,4-diazacycloheptyl or [1,5]-diazocanyl ring which is optionally substituted by hydroxyl, carboxyl, linear or branched acyl or alkoxycarbonyl, each of which has up to 5 carbon atoms, phenyl or linear or branched alkyl having up to 5 carbon atoms, which can in turn be substituted by hydroxyl, carboxyl, ureido, linear or branched alkoxy, acylamino or alkoxycarbonyl, each of which has up to 4 carbon atoms, or a group of the formula —(O)$_d$—(CO)$_e$—NR$^{14}$R$^{15}$, wherein d is the number 0 or 1, e is the number 0 or 1, and R$^{14}$ and R$^{15}$ are identical or different and are hydrogen or linear or branched alkyl having up to 4 carbon atoms, and/or the heterocycles are optionally substituted by a radical of the formula —(CO)$_f$—NR$^{16}$R$^{17}$ or —(O)$_{d'}$—(CO)$_{e'}$—NR$^{14'}$R$^{15'}$, wherein f is as defined above for e and is identical thereto or different therefrom, R$^{16}$ and R$^{17}$ are identical or different and are as defined above for R$^{14}$ and R$^{15}$, and d', e$^{40}$, R$^{14'}$ and R$^{15'}$ are identical or different and are defined above d, e, R$^{14}$ and R$^{15}$ and R$^3$, R$^4$, R$^5$ and R$^6$ are identical or different and are hydrogen or linear or branched alkyl having up to 7 carbon atoms which is optionally substituted by hydroxyl, fluorine or a radical of the formula —NR$^{18}$R$^{19}$, wherein R$^{18}$ and R$^{19}$ are identical or different and are as defined above for R$^{14}$ and R$^{15}$, or R$^3$ and R$^4$ and/or R$^5$ and R$^6$, in each case together with the nitrogen atom, form a morpholine, piperazinyl, piperidinyl or pyrrolidinyl ring, with the proviso that if R$^3$, R$^4$, R$^5$ and R$^6$ are hydrogen, R$^1$, R$^2$ and L together with the two nitrogen atoms, must not be piperazinyl or 1,4-diazacycloheptyl, provided that if R$^1$, R$^2$ and L together with the 2 nitrogen atoms are a piperazinyl radical, A, A', D, D', E and E' are not hydrogen or alkoxy and their salts.

3. 2,2'-Bridged bis-2,4-diaminoquinazolines of the formula according to claim 1 in which A, A', D, D', E and E' are identical or different and are hydrogen, fluorine, chlorine, nitro, trifluoromethyl, trifluoromethoxy or linear or branched alkyl having up to 3 carbon atoms, L is a linear or branched alkylene chain having up to 10 carbon atoms which is optionally interrupted by an oxygen or sulphur atom or by a group of the formula —NR$^7$, wherein R$^7$ is hydrogen or linear or branched alkyl having up to 3 carbon atoms, and where the alkylene chain is optionally substituted by up to 2 identical or different substituents selected from hydroxyl, linear or branched alkoxy having up to 3 carbon atoms, phenyl, benzyloxy, phenoxy and pyridyl, it being possible for the rings in turn to be substituted by fluorine, chlorine, bromine, hydroxyl, cyano, linear or branched alkoxy having up to 3 carbon atoms, or a radical of the formula —(NH)$_a$—CONR$^8$R$^9$, wherein R$^8$ and R$^9$ are identical or different and are hydrogen or linear or branched alkyl having up to 3 carbon atoms, and a is the number 0 or 1, R$^1$ and R$^2$ are identical or different and are hydrogen or linear or branched alkyl having up to 3 carbon atoms which is optionally substituted by hydroxyl, fluorine or a radical of the formula —NR$^{12}$R$^{13}$, wherein R$^{12}$ and R$^{13}$ are identical or different and are hydrogen or linear or branched alkyl having up to 4 carbon atoms, or R$^1$, R$^2$ and L, together with the two nitrogen atoms, form a 2,3,4,5-tetrahydro-1H-benzo-[1,4]diazepine, 1,4-diazacycloheptyl or [1,5]-diazocanyl ring which is optionally substituted by hydroxyl, carboxyl, linear or branched acyl or alkoxycarbonyl, each of which has up to 4 carbon atoms, phenyl or linear or branched alkyl having up to 4 carbon atoms, which in turn can be substituted by hydroxyl, carboxyl, ureido, linear or branched alkoxy, acylamino or alkoxycarbonyl, each of which has up to 3 carbon atoms, or a group of the formula —(O)$_d$—(CO)$_e$—NR$^{14}$R$^{15}$, wherein d is the number 0 or 1, e is the number 0 or 1, and R$^{14}$ and R$^{15}$ are identical or different and are hydrogen or linear or branched alkyl having up to 3 carbon atoms, and/or the heterocycles are optionally substituted by a radical of the formula —(CO)$_f$—NR$^{16}$R$^{17}$ —(O)$_{d'}$—(CO)$_{e'}$—N$^{14'}$R$^{15'}$, wherein f is as defined above for e and is identical thereto or different therefrom, R$^{16}$ and R$^{17}$ are identical or different and are as defined above for R$^{14}$ and R$^{15}$, and d', e', R$^{14}$ and R$^{15}$ are identical or different and are as defined above d, e, R$^{14}$ and R$^{15}$ and R$^3$, R$^4$, R$^5$ and R$^6$ are identical or different and are hydrogen or linear or branched alkyl having up to 5 carbon atoms which is optionally substituted by hydroxyl, fluorine or a radical of the formula —NR$^{18}$R$^{19}$, wherein R$^{18}$ and R$^{19}$ are identical or different and are as defined above for R$^{14}$ and R$^{15}$, or R$^3$ and R$^4$ and/or R$^5$ and R$^6$, in each case together with the nitrogen atom, form a morpholine, piperazinyl, piperidinyl or pyrrolidinyl ring with the proviso that if R$^3$, R$^4$, R$^5$ and R$^6$ are hydrogen, R$^1$, R$^2$ and L, together with the two nitrogen atoms, must not be piperazinyl or 1,4-diazacycloheptyl, provided that if R$^1$, R$^2$ and L together with the 2 nitrogen atoms are a piperazinyl radical, A, A', D, D', E and E' are not hydrogen or alkoxy and their salts.

4. A method of treating diseases of the central nervous system which comprises administering an effective amount of a compound according to claim 1 to a host in need thereof.

5. The method according to claim 4, wherein the disease is dementia.

6. The method according to claim 4 wherein said disease is depression.

7. The method according to claim 4 wherein said disease is myotonic dystrophy.

8. The method according to claim 4 wherein said disease is asthma.

9. A pharmaceutical composition comprising a therapeutically effective amount of a compound according to claim 1 and a biocompatible formulation aid.

10. 2,2'-Bridged bis-2,4-diaminoquinazolines of the general formula (I'):

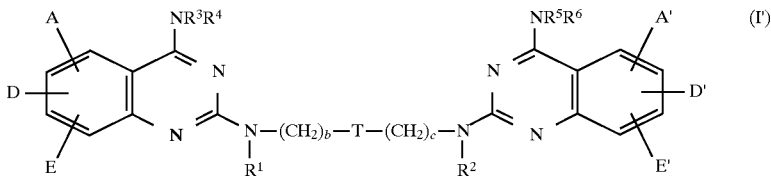

in which

A, A', D, D', E and E' are identical or different and are hydrogen, halogen, hydroxyl, nitro, trifluoromethyl, trifluoromethoxy or linear or branched alkyl or alkoxy, each of which has up to 6 carbon atoms, b and c are identical or different and are the number 0, 1, 2, 3, 4 or 5, and T is cycloalkyl having 3 to 6 carbon atoms, aryl having 6 to 10 carbon atoms or a 3- to 8-membered, saturated or unsaturated, optionally benzo-fused and/or heterocyclically or carbocyclically bridged heterocycle having up to 3 heteroatoms from the soup comprising S, N and/or O, wherein all the ring systems are optionally substituted by up to 3 identical or different substituents selected from halogen, cyano, hydroxyl, nitro, carboxyl, linear or branched alkyl, alkoxycarbonyl or alkoxy, each of which has up to 9 carbon atoms, and a radical of the formula —CO—NR$^{10}$R$^{11}$, wherein R$^{10}$ and R$^{11}$ are identical or different and are hydrogen or linear or branched alkyl having up to 6 carbon atoms, R$^1$ and R$^2$ are identical or different and are hydrogen, phenol or linear or branched alkyl having up to 6 carbon atoms which is optionally substituted by hydroxyl, halogen or a radical of the formula —NR$^{12}$R$^{13}$, wherein R$^{12}$ and R$^{13}$ are identical or different and are as defined above for R$^{10}$and R$^{11}$, or, in the case where b is the number 0 and c is as defined above T and R$^1$ together with the nitrogen atom, form a 3- to 8-membered, optionally benzo-fused and/or heterocyclically or carbocyclically bridged, saturated heterocycle having up to 2 heteroatoms from the group comprising S, N and/or O, and R$^3$, R$^4$, R$^5$ and R$^6$ are identical or different and are hydrogen, phenyl or linear or branched alkyl having up to 8 carbon atoms which is optionally substituted by hydroxyl, halogen or a radical of the formula —NR$^{18}$R$^{19}$, wherein R$^{18}$ and R$^{19}$ are identical or different and are as defined above for R$^{10}$ and R$^{11}$, or R$^3$ and R$^4$ and/or R$^5$ and R$^6$, in each case together with the nitrogen atom, form a 5- to 7-membered saturated heterocycle which can optionally contain up to 2 further heteroatoms from the group comprising S and O, or a radical of the formula —NR$^{20}$, wherein R$^{20}$ is as defined above for R$^7$ and is identical thereto or different therefrom, and their salts.

11. 2,2'-Bridged bis-2,4-diaminoquinazolines of the formula according to claim 10 in which A, A', D, D', E and E' are identical or different and are hydrogen, fluorine, chlorine, bromine, hydroxyl, nitro, trifluoromethyl, trifluoromethoxy or linear or branched alkyl or alkoxy, each of which has up to 4 carbon atoms, b and c are identical or different and are the number 0, 1, 2, 3 or 4, and T is cyclopropyl, cyclobutyl, cyclopentyl, cyclohexyl, cycloheptyl, phenyl, naphthyl, pyridyl, quinolyl, isoquinolyl, morpholinyl or piperidinyl which is optionally substituted by up to 2 identical or different substituents selected from fluorine, chlorine, bromine, cyano, hydroxyl, carboxyl, linear or branched alkyl, alkoxycarbonyl or alkoxy, each of which has up to 7 carbon atoms, and a radical of the formula —CO—NH$_2$, R$^1$ and R$^2$ are identical or different and are hydrogen or linear or branched alkyl having up to 3 carbon atoms which is optionally substituted by hydroxyl, fluorine or a radical of the formula —NR$^{12}$R$^{13}$, wherein R$^{12}$ and R$^{13}$ are identical or different and are hydrogen or linear or branched alkyl having up to 5 carbon atoms, or, in the case where b is the number 0 and c is as defined above, T and R$^1$ together with the nitrogen atom, form a piperidine, morpholine, pyrrolidine or 4-azatricyclo [5.2.2.0]-2,6-undecenyl ring, and R$^3$, R$^4$, Rs and R$^6$ are identical or different and are hydrogen or linear or branched alkyl having up to 7 carbon atoms which is optionally substituted by hydroxyl, fluorine or a radical of the formula —NR$^{18}$R$^{19}$, wherein R$^{18}$ and R$^{19}$ are identical or different and are hydrogen or linear or branched alkyl having up to 4 carbon atoms, or R$^3$ and R$^4$ and/or R$^5$ and R$^6$, in each case together with the nitrogen atom, form a morpholine, piperazinyl, piperidinyl or pyrrolidinyl ring, and their salts.

12. 2,2'-Bridged bis-2,4-diaminoquinazolines of the formula according to claim 10 in which
A, A', D, D', E and E' are identical or different and are hydrogen, fluorine, chlorine, nitro, trifluoromethyl, trifluoromethoxy or linear or branched alkyl having up to 3 carbon atoms,
b and c are identical or different and are the number 0, 1, 2, 3 or 4,
and
T is cyclopropyl, cyclobutyl, cyclopentyl, cyclohexyl, cycloheptyl, phenyl, pyridyl or piperidinyl which is optionally substituted by fluorine, chlorine, bromine, cyano, hydroxyl, carboxyl, linear or branched alkyl, alkoxycarbonyl or alkoxy, each of which has up to 5 carbon atoms, or a radical of the formula —CO—NH$_2$,
$R^1$ and $R^2$ are identical or different and are hydrogen or linear or branched alkyl having up to 3 carbon atoms which is optionally substituted by hydroxyl, fluorine or a radical of the formula —NR$^{12}$R$^{13}$,
wherein
$R^{12}$ and $R^{13}$ are identical or different and are hydrogen or linear or branched alkyl having up to 4 carbon atoms,
or, in the case where b is the number 0 and c is as defined above T and $R^1$ together with the nitrogen atom, form a piperidine, pyrrolidine or 4-azatricyclo[5.2.2.0]-2,6-undecenyl ring,
and
$R^3$, $R^4$, $R^5$ and $R^6$ are identical or different and are hydrogen or linear or branched alkyl having up to 5 carbon atoms Which is optionally substituted by hydroxyl, fluorine or a radical of the formula —NR$^{18}$R$^{19}$,
wherein
$R^{18}$ and $R^{19}$ are identical or different and are hydrogen or linear or branched alkyl having up to 3 carbon atoms, or
$R^3$ and $R^4$ and/or $R^5$ and $R^6$, in each case together with the nitrogen atom, form a morpholine, piperazinyl, piperidinyl or pyrrolidinyl ring
and their salts.

13. A method of treating diseases of the central nervous system which comprises administering an effective amount of a compound according to claim 10 to a host in need thereof.

14. The method according to claim 13, wherein the disease is dementia.

15. The method according to claim 13, wherein the disease is depression.

16. The method according to claim 13, wherein said disease is myotonic dystrophy.

17. The method according to claim 13, wherein said disease is asthma.

18. A pharmaceutical composition comprising a therapeutically effective amount of a compound according to claim 10 and a biocompatible formulation aid.

* * * * *

UNITED STATES PATENT AND TRADEMARK OFFICE
CERTIFICATE OF CORRECTION

PATENT NO. : 5,874,438
DATED : February 23, 1999
INVENTOR(S) : Schohe-Loop, et al It is certified that error appears in the above-indentified patent and that said Letters Patent is hereby corrected as shown below:

| | |
|---|---|
| Col. 23, line 41 | Delete " enrich " and substitute -- which -- |
| Co. 23, line 51 | Delete " carbonyl " and substitute -- carboxyl -- |
| Col. 23, line 55 | Delete " carbon?l " and substitute -- carboxyl -- |
| Col. 24, line 50 | Delete " pryidazinyl " and substitute -- pyridazinyl -- |
| Col. 25, line 29 | Delete " $e^{40}$ " and substitute -- e' -- |
| Col. 27, line 40 | Delete " soup " and substitute -- group -- |
| Col. 27, line 52 | Delete " phenol " and substitute -- phenyl -- |
| Col. 28, line 57 | Delete " Rs " and substitute -- $R^5$ -- |

Signed and Sealed this

Twelfth Day of October, 1999

Attest:

Q. TODD DICKINSON

*Attesting Officer*   *Acting Commissioner of Patents and Trademarks*